United States Patent [19]
Grim

[11] Patent Number: 6,056,712
[45] Date of Patent: May 2, 2000

[54] MULTI-FUNCTIONAL ORTHOSIS FOR THE FOOT, HEEL, ANKLE AND LOWER LEG

[76] Inventor: Tracy E. Grim, 3010 W. Boston Ct., Broken Arrow, Okla. 74012

[21] Appl. No.: 08/927,836

[22] Filed: Sep. 11, 1997

Related U.S. Application Data

[63] Continuation of application No. 08/551,157, Oct. 31, 1995, abandoned.

[51] Int. Cl.[7] ........................................................ A61F 5/00
[52] U.S. Cl. ................................. 602/27; 602/23; 602/16
[58] Field of Search ................................. 602/5–8, 9, 10, 602/16, 23, 27–29; 128/882

[56] References Cited

U.S. PATENT DOCUMENTS

| | | |
|---|---|---|
| Re. 33,762 | 12/1991 | Lonardo . |
| D. 317,651 | 6/1991 | Farris et al. . |
| D. 326,948 | 6/1992 | Williams et al. . |
| 3,345,654 | 10/1967 | Noble . |
| 3,732,861 | 5/1973 | Lehneis ................................. 128/80 E |
| 3,976,059 | 8/1976 | Lonardo . |
| 4,573,457 | 3/1986 | Parks ........................................ 602/29 |
| 4,848,326 | 7/1989 | Lonardo . |
| 4,869,267 | 9/1989 | Grim et al. . |
| 4,926,884 | 5/1990 | Lonardo . |
| 4,953,569 | 9/1990 | Lonardo . |
| 4,964,402 | 10/1990 | Grim et al. . |
| 5,020,523 | 6/1991 | Bodine . |
| 5,052,128 | 10/1991 | Lonardo . |
| 5,078,128 | 1/1992 | Grim et al. ............................ 128/83.5 |
| 5,088,480 | 2/1992 | Wang . |
| 5,092,319 | 3/1992 | Grim . |
| 5,115,627 | 5/1992 | Scott . |
| 5,143,058 | 9/1992 | Luber et al. . |
| 5,151,081 | 9/1992 | Williams . |
| 5,154,695 | 10/1992 | Farris et al. . |
| 5,163,196 | 11/1992 | Graebe et al. . |
| 5,176,623 | 1/1993 | Stetman et al. ........................... 602/27 |
| 5,224,925 | 7/1993 | Varn . |
| 5,269,748 | 12/1993 | Lonardo . |
| 5,275,179 | 1/1994 | Lonardo . |
| 5,282,483 | 2/1994 | Wang . |
| 5,329,705 | 7/1994 | Grim et al. . |
| 5,352,189 | 10/1994 | Schumann et al. .................. 602/27 X |
| 5,364,162 | 11/1994 | Bar et al. . |
| 5,368,551 | 11/1994 | Zuckerman ............................ 602/27 X |
| 5,372,576 | 12/1994 | Hicks .................................... 602/23 X |
| 5,421,822 | 6/1995 | Wang ........................................ 602/27 |
| 5,431,624 | 7/1995 | Saxton et al. ......................... 602/28 X |
| 5,433,695 | 7/1995 | Drennan ..................................... 602/10 |
| 5,453,082 | 9/1995 | Lamont ................................. 128/882 X |
| 5,486,157 | 1/1996 | DiBenedetto .......................... 602/28 X |
| 5,520,627 | 5/1996 | Malewicz .............................. 602/27 X |
| 5,545,127 | 8/1996 | DeToro ..................................... 602/27 |
| 5,689,845 | 11/1997 | Sobieralski . |

*Primary Examiner*—Richard J. Apley
*Assistant Examiner*—Jayne Saydah
*Attorney, Agent, or Firm*—Lyon & Lyon LLP

[57] ABSTRACT

A multi-function orthosis for immobilizing the lower leg, heel, ankle and foot of a human patient, which also provides adjustable therapeutic pressure on the foot sole, and which allows for ambulation. An upper, leg unit lined with a pneumatic bladder is adapted to receive the lower leg of the patient and is hingedly attached to a lower, foot base unit which is adapted to receive the foot of the patient. Retractable kickstands attached to the foot base unit extend to prevent outward or inward rolling of the patient's foot, leg and hip, and to also provide protection from the bedding. An extendable foot slide adjusts to support the foot of the patient and to retract when not in use, and an adjustable and retractable toe flap is attached to the foot slide to protect the toes when the patient is immobilized or ambulatory. A low-profile ambulation sled attachable to the bottom of the foot base unit provides a relatively wide platform to allow safe ambulation of the patient without the removal of the orthosis or the aid of other devices.

2 Claims, 11 Drawing Sheets

MULTI-FUNCTIONAL ORTHOSIS FOR THE FOOT, HEEL, ANKLE AND LOWER LEG

This application is a Continuation Application of application Ser. No. 08/551,157 filed on Oct. 31, 1995, now abandoned.

BACKGROUND OF THE INVENTION

1. Field of the Invention

The field of the invention generally relates to orthotic devices, and more particularly to a multi-function orthosis for the foot, heel, ankle and lower leg.

2. Description of the Related Art

Numerous types of devices intended to immobilize the lower leg and foot of a human patient are available. Examples of simple devices such as casts or splints are well known in the art. Other more recent devices provide certain limited immobilization and protection benefits but, because of their design, do not provide protection against immobilization problems such as decubitus ulcers (pressure sores) as does the present invention.

Accordingly, there is a need for a multi-function orthosis for the foot, heel, ankle and lower leg which provides three-dimensional immobilization and protection benefits, minimizes the risk of pressure sores on the heel and posterior portion of the lower leg, provides a range of therapeutic pressures and positions for the foot, yet still allows ambulation of the patient without removal of the device.

The present invention constitutes an improvement over the prior art in that it provides three dimensional support of the foot, lower leg, and hip of an immobilized patient, and further provides a significant range of therapeutic pressure on the sole of the patient's foot for treatment of muscle contractures or other spastic afflictions. The present invention still further allows for ambulation without the need for another device such as an outer shoe.

SUMMARY OF THE INVENTION

The present invention is directed to an orthosis having an upper, leg unit and a lower, foot base unit rotatably attached together for immobilization of the ankle.

In a first, separate aspect of the invention, the orthosis has a telescoping foot slide attached to the anterior portion of the lower, foot base unit.

In a second, separate aspect of the invention, the telescoping foot slide has an adjustable toe flap for protecting the patient's toes.

In a third, separate aspect of the present invention, the orthosis employs the use of one or more adjustable kickstands attached to the foot base unit to provide three dimensional support of the hip and leg by preventing outward or inward roll of the foot of bed-ridden patients, and for maintaining bedding in a spaced relation to the patient's foot and lower leg.

In a fourth, separate aspect of the present invention, the orthosis has an attachable, low-profile sled which can be attached without removal of the device and provides a relatively wide platform for safe ambulation of the patient without the use of other devices such as shoes.

In a fifth, separate aspect of the present invention, the orthosis has a pneumatic bladder lining the upper, leg unit.

DESCRIPTION OF THE DRAWINGS

FIG. 7 is a side view of the toe slide.

DETAILED DESCRIPTION OF THE PREFERRED EMBODIMENT

A preferred embodiment will now be described with respect to the drawings. Like elements appearing in multiple figures are similarly numbered.

Figures 16, 16A:
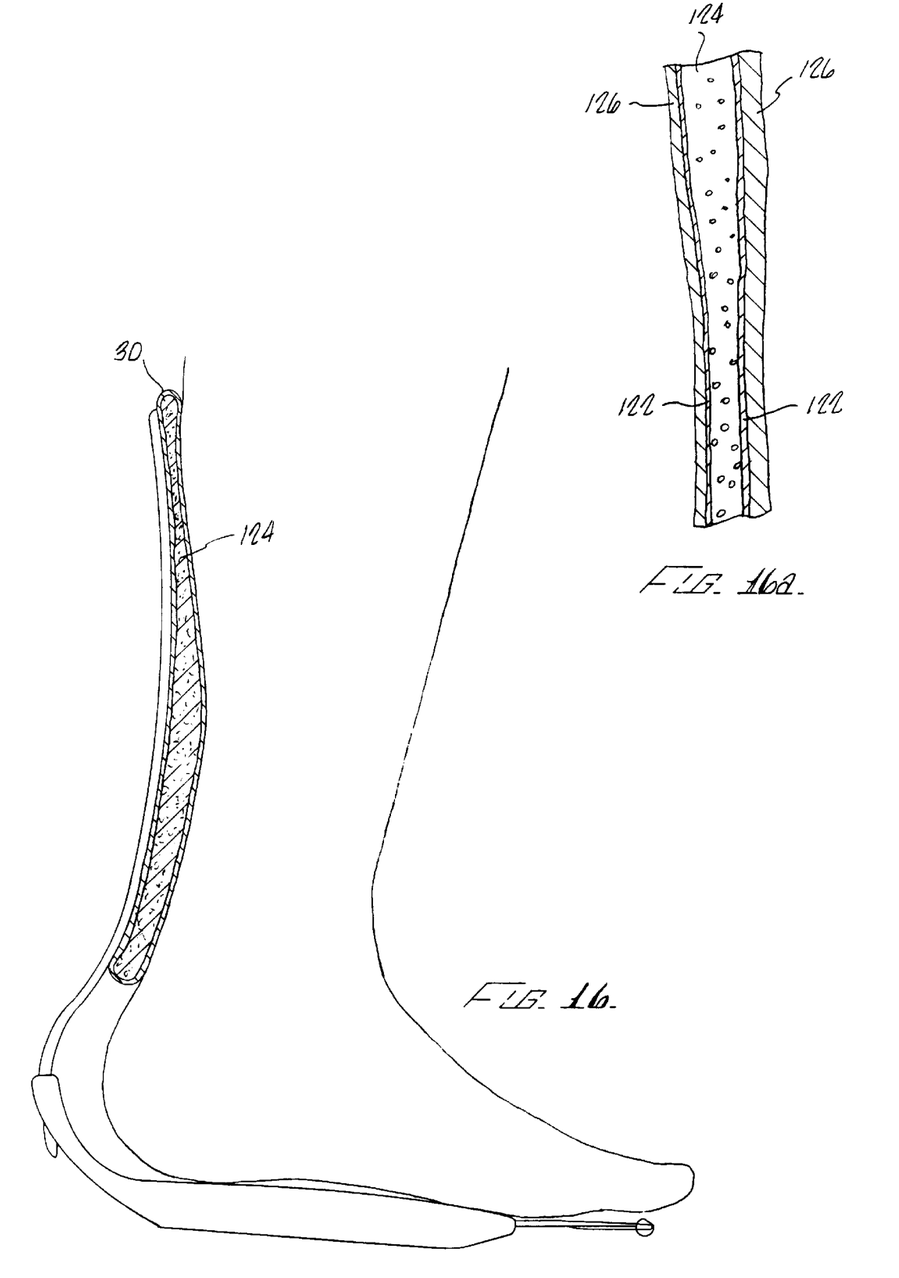
FIGS. 16 and 16a are side cross-sectional views of the upper unit and attached pneumatic bladder.

Referring to FIGS. 1–4, the orthosis 5 of the present invention may generally comprise an upper, leg unit 10, which is adapted to receive the lower leg and calf area of the patient, and a lower, foot base unit 20 which supports the foot. Either of the upper, leg unit 10 or lower, foot base unit 20 may be fitted with a pneumatic bladder 30 (as shown in FIGS. 16 and 16a) for increased comfort and support. Bladder 30 also provides greater protection against decubitus ulcers (pressure sores) by reducing peak pressure points between the patient's skin and the orthosis 5. The orthosis 5 of the present invention may be attached to the patient's foot and lower leg through the use of a softgood 40 and attachment strap 42. The softgood 40 can be attached to the foot base unit 20 through the use of fasteners 44 that fit into slots 46 and are fastened through the use of upper unit 10 may also include an access panel or other similar means.

Figure 5:
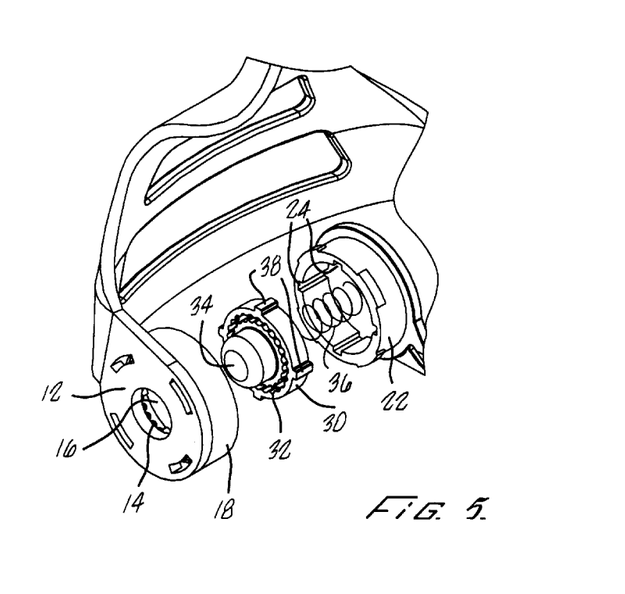
FIG. 5 is an exploded view of the hinge area.

Referring also now to FIG. 5, the upper unit 10 and the foot base unit 20 may be joined by upper unit gears 12, foot base unit gears 22, and middle gears 30 which together preferably act as adjustable hinge mechanisms. Upper unit gear 12 includes gear teeth 14 which are adapted to receive gear holes 32 of middle gear 30. Gear button 34 fits into and through upper unit gear hole 16, and is preferably spring loaded into a locked position by spring 36 which is housed between gear 30 and foot base unit gear 22. Middle gear 30 has gear flanges 38 which are adapted to fit into foot base unit recesses 24 to prevent movement of the gear 30 in relation to the foot base unit 20. Hinge guards 18 protect middle gears 30 and preferably prevent unintended actuation of the hinge mechanism. The relative angle between the upper unit 10 and foot base unit 20 can be adjusted by simultaneously pressing the gear button 34 on each side of the orthosis 5 to disengage upper unit gear teeth 14 from gear holes 32, thereby allowing angular adjustment of the base unit 20 in relation to the upper unit 10. Once the desired relative angle is reached, the gear buttons 34 on each side can be released, locking the gears into place.

In a preferred embodiment, the gears are preformed to allow the relative angle between the upper unit 10 and foot base unit 20 to be set at, for example, a right angle of 90 degrees, or at more acute or obtuse angles, in predetermined increments to allow for specific therapeutic applications. As a safety precaution, it is preferred that both gear buttons 34 be required to be simultaneously pressed to allow movement of the hinges, which prevents hinge activation from accidental blows or pressure from items such as furniture, etc. Any other type of locking hinge mechanism or hinge design may also be employed on one or both sides of the orthotic device.

Preferably, orthosis 5 and its hinge mechanism may also be designed to fit onto the foot when upper unit 10 and foot base unit 20 are configured at a wide angle position relative to each other. This is beneficial for patients having drop foot or other similar disorders. As the patient's range of motion increases, the orthosis 5 may preferably be periodically and incrementally adjusted, thereby allowing the foot disorder to be treated with variable pressure over time. This capability is an advance over the prior art devices, which are typically rigidly constructed in a uniform "L"-shaped configuration that maintains a 90 degree relation between the calf support and the foot support. Providing variable foot sole pressure allows doctors, therapists and other practitioners to easily place the foot in incremental degrees of pressure over time without removing the orthosis 5. This variable pressure may also help prevent flexion contractures in the lower leg that are common in patients who are bedridden.

Figure 8:
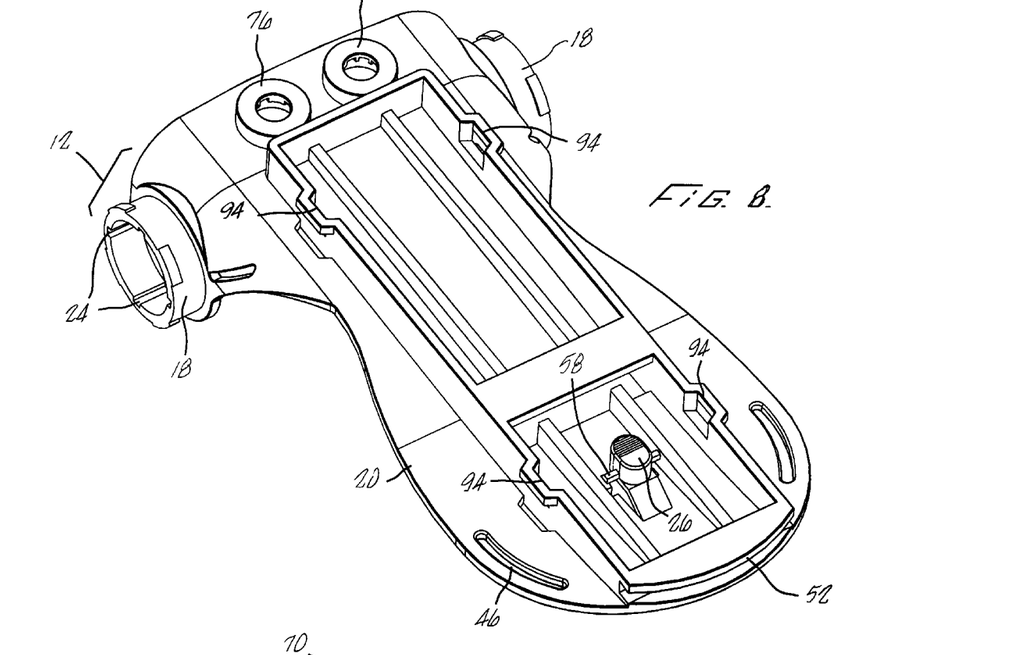
FIG. 8 is a bottom perspective view of the foot base unit.

Referring now to FIGS. 1–4, 6 and 7, it is preferred that foot slide 50 be movably attached to the foot base unit 20 at the foot slide opening 52. The posterior portion of the foot slide 50 may be fully retracted into the foot base unit 20 at the foot slide opening 52 when placing the device onto a patient's foot or when orthosis 5 is not in use. It is preferred that foot slide 50 also be telescopically extended outwardly to provide a surface area 54 to support the sole and toes of the patient's foot. The foot slide 50 may be actuated by the use of slide button 26 (as shown in FIG. 8), which is located on the bottom of foot base unit 20. Slide button 26 has protruding bars 58 which are adapted to fit into slide slots 56, and thereby prevent movement of the foot slide 50. To advance or retract the foot slide 50, a physician or other qualified person may press the slide button 26 to disengage protruding bars 58 from the slide slots 56. The operator may then move the foot slide 50 to the desired location, then release the slide button 26, thereby placing protruding bars 58 into new slide slots 56.

Figure 6:
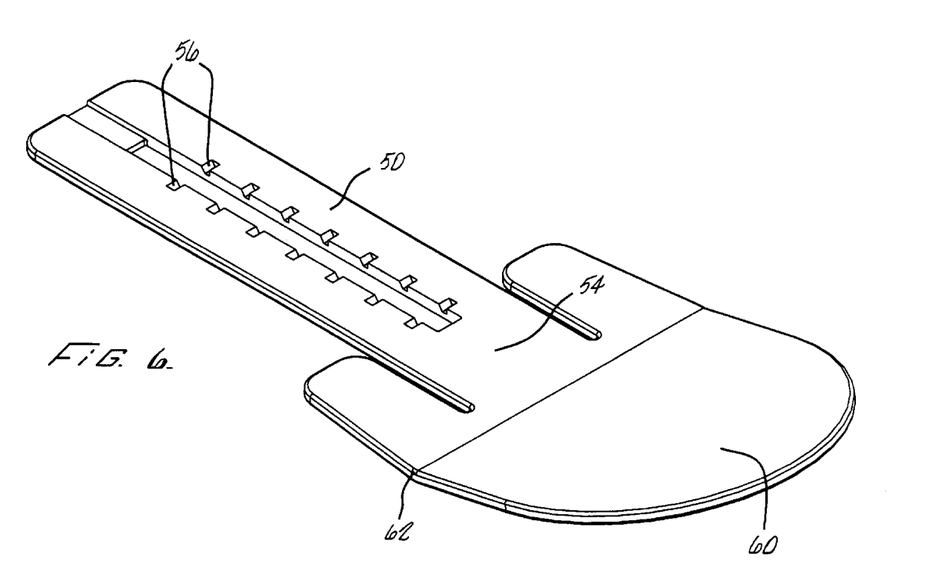
FIG. 6 is a perspective view of the toe slide.

At the anterior portion of the foot slide 50 is toe flap 60. The toe flap 60 may either be in a fixed position in relation to foot slide 50 or may be adjustable through the use of a toe flap hinge 62. Toe flap hinge 62 can be adapted to receive a bar (not shown) or other hinge mechanism which attaches the toe flap 60 to the foot slide 50 in a hinge like fashion. In a hinged embodiment, the toe flap 60 may be radially adjusted from a full retracted position where it may rest on top of the foot slide 50. When extended, the toe flap 60 may also be used to protect the patient's toes during ambulation or from bedding during convalescence. The toe flap hinge 62 may also contain an outer lip (not shown) that prevents radial adjustment of the toe flap 60 beyond, for example, 180 degrees in relation to the foot slide 50 to a position unsafe for ambulation.

Figure 9:
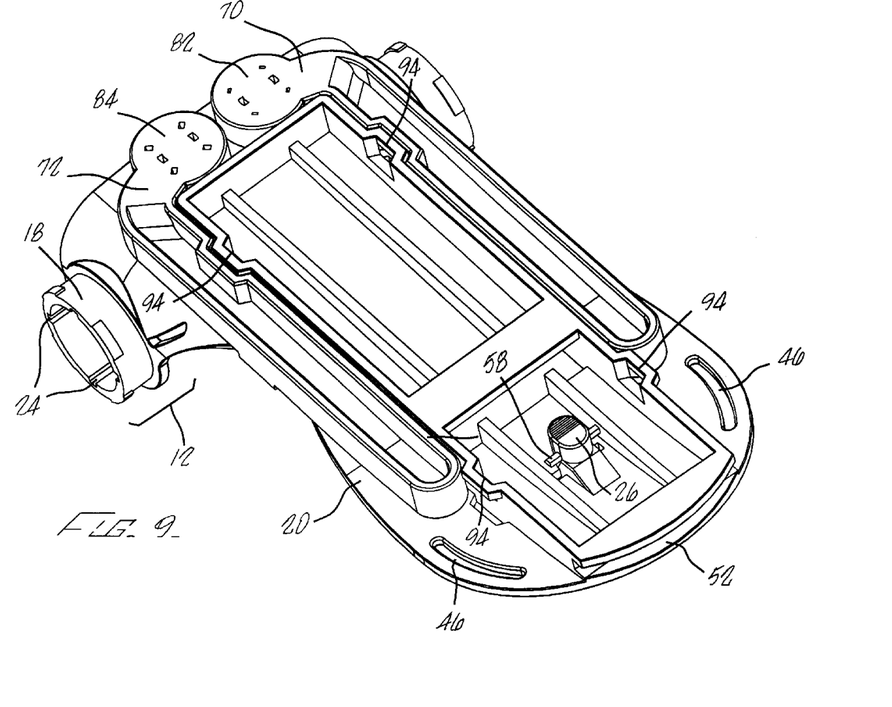
FIG. 9 is a bottom perspective view of the foot base unit with the kickstands attached.
Figure 10:
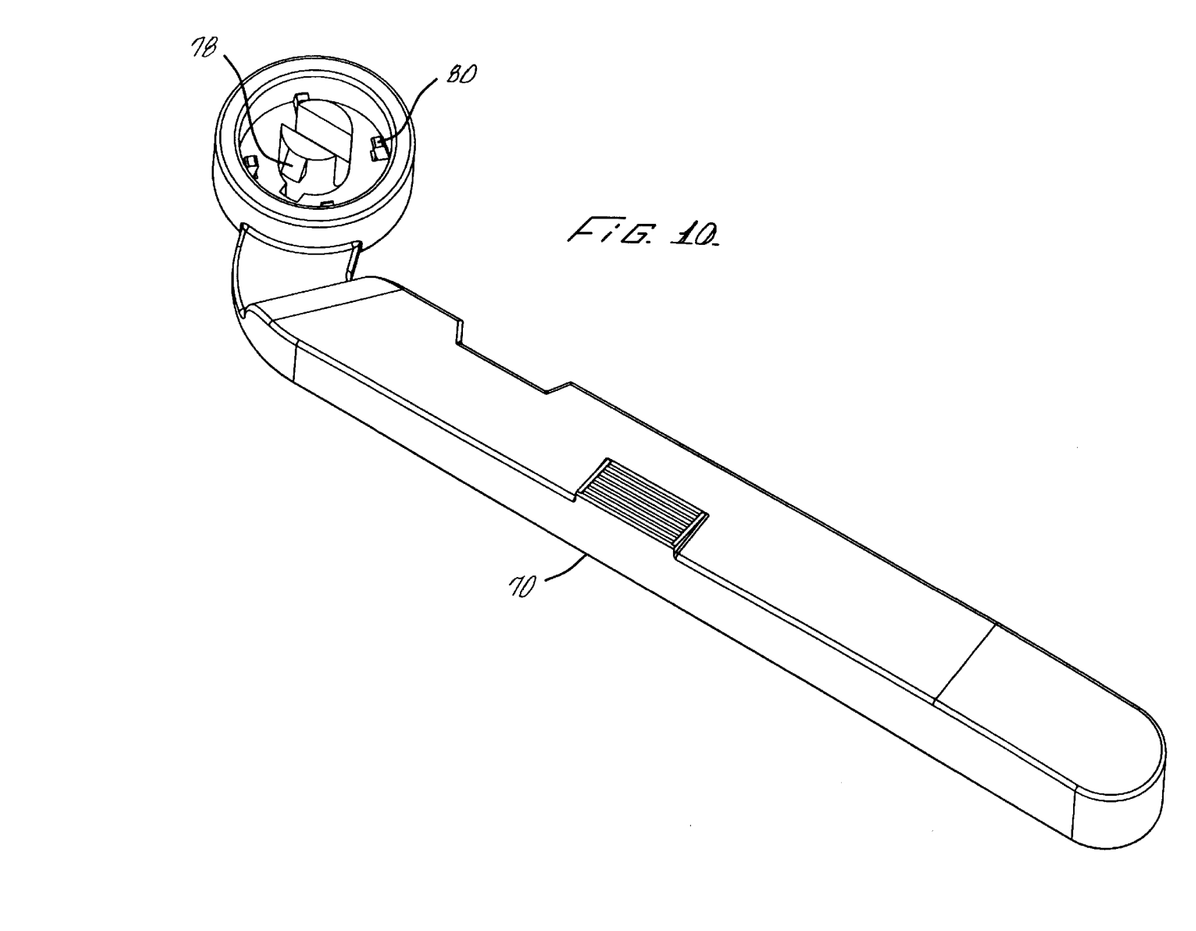
FIG. 10 is a perspective view of a kickstand.

Referring now to FIGS. 8–10, kickstands 70 and 72 may be attached to kickstand hinges 74 and 76, located on the bottom of foot base unit 20. The kickstand hinges 74 and 76 may include kickstand gear teeth 78 which are received by kickstand hinges 74 and 76. The kickstands 70 and 72 may be spring locked into a locked position by the use of a kickstand spring mechanism 80. By pressing the kickstands 70 and 72 against the foot base unit 20, the kickstand gear teeth 78 may be disengaged from the kickstand hinges 74 and 76, and adjusted to the desired position, by pressing the kickstand base portions 82 and 84 to disengage the kickstand spring mechanism 80. The kickstands 70 and 72 may then be radially adjusted outwardly from the foot base unit 20 to a 90 degree angle or beyond in relation thereto. During ambulation or while not in use, the kickstands 70 and 72 may be housed adjacent and below the foot base unit 20, as shown in FIG. 9. While a patient is bedridden and in the supine position, the kickstands 70 and 72, when extended, preferably do not allow an outward or inward roll of the patient's foot, leg and hip, which helps keep the patient from developing pressure sores on the lateral or interior aspects of the lower limbs. When extended, the kickstands 70 and 72 may also provide a tent pole effect to the bedding for patients laying on their side, thus further protecting against sheet burn.

Referring now to FIGS. 1, 4, 8, 9, 11, 12 and 13, a sled 90 may be attached to the bottom of the foot base unit 20 through the use of sled latch teeth 92. Sled latch teeth 92 are preferably received by foot base unit slots 94 located on the bottom of foot base unit 20 (as shown in FIGS. 8 and 9). The sled 90 may be detached from the foot base unit 20 by pressing release buttons 96 which, when pushed, release sled latch teeth 92 from foot base unit slots 94. The sled 90 preferably has a low profile, is relatively wide, and has an upward curving front portion 98 to provide a safe platform for ambulation.

Figure 11:
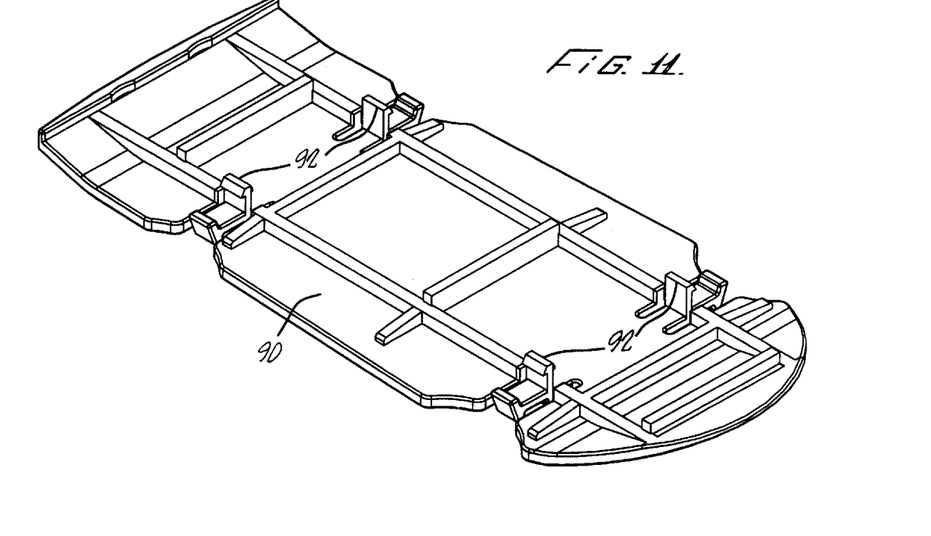
FIG. 11 is a perspective view of the sled.
Figure 12:
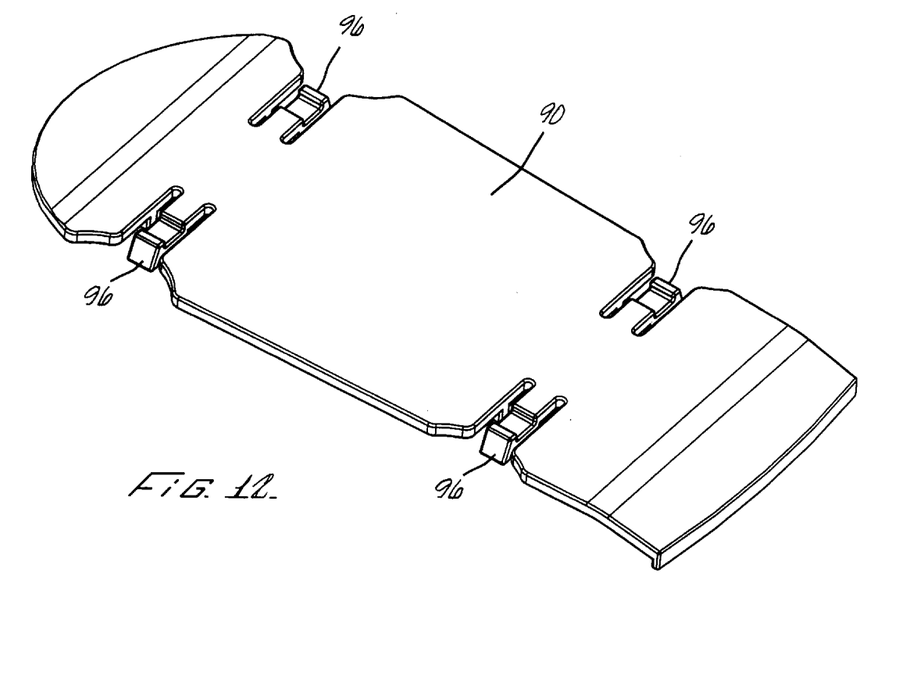
FIG. 12 is a bottom perspective view of a sled.
Figure 13:
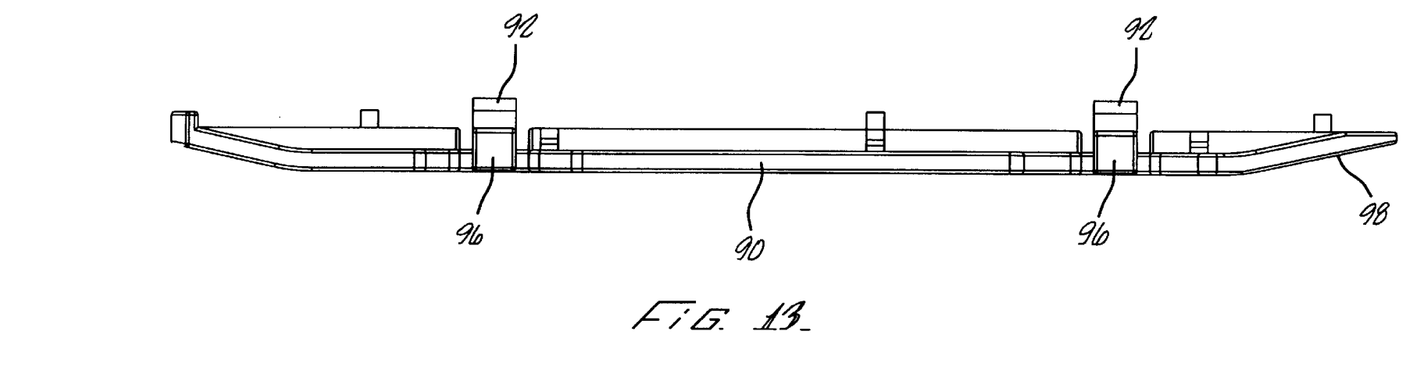
FIG. 13 is a side view of the sled.

The sled 90 may be attached to the foot base unit 20 to provide for ambulation without removal of the orthosis 5 from the patient and without the aid of other devices like shoes, slippers or some other device. The sled 90 may be removed from the foot base unit, again without the need to remove the orthosis 5, to provide access to the kickstand base portions 82 and 84 or for cleaning. As a safety precaution to prevent actuation of the kickstands during ambulation, the sled 90 preferably covers the kickstand hinges base portions 82 and 84 while in place. The sled 90 may also remain attached to the foot base unit 20 for patients suffering from senility and dimensia, which patients may otherwise ambulate without aid or permission.

Figures 14, 15:
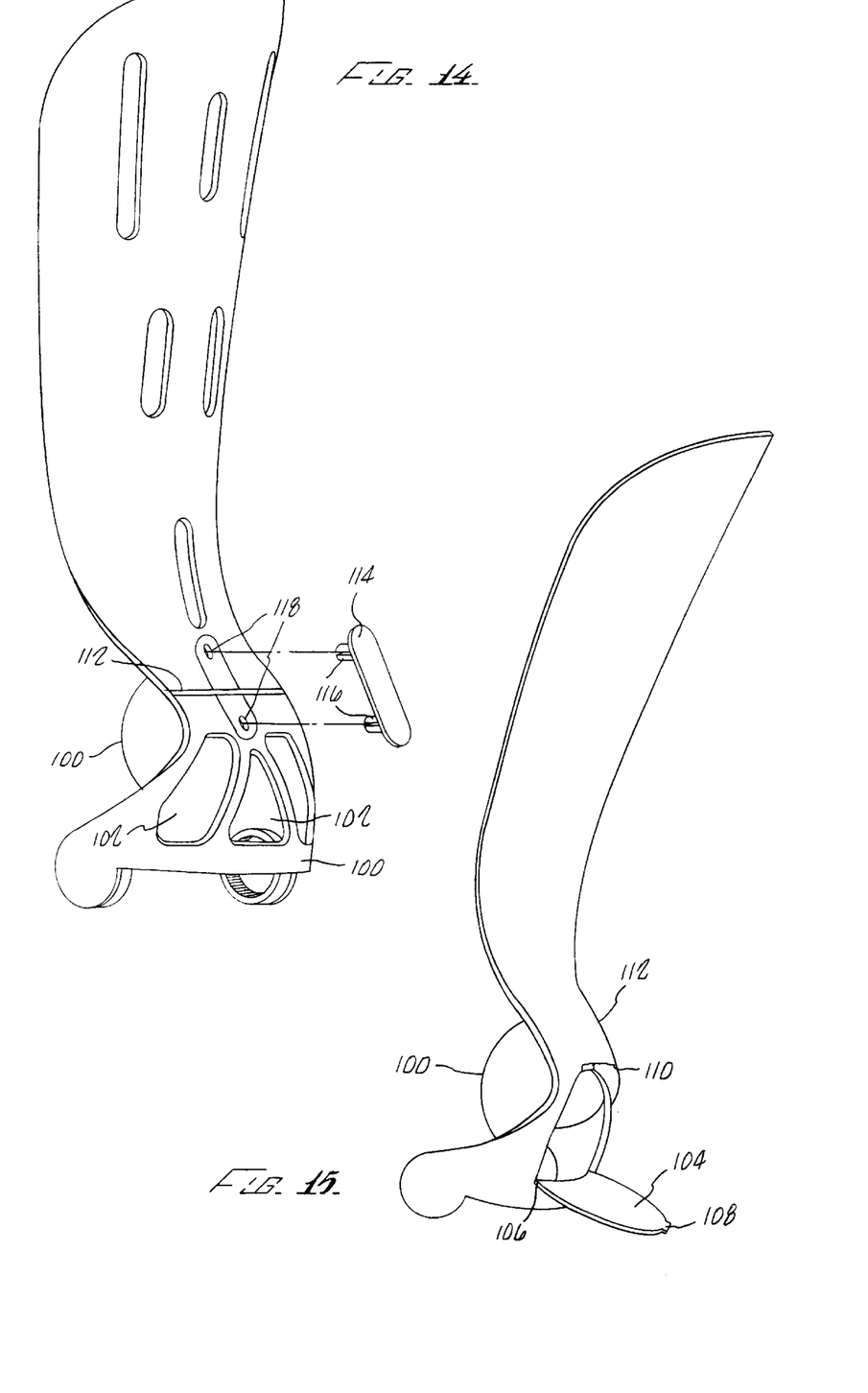
FIG. 14 is a rear perspective view of the upper unit.
FIG. 15 is a rear perspective view of the upper unit.

Now referring to FIGS. 14 and 15, the lower area 100 of upper unit 10 is preferably recessed to avoid contact with the patient's heel. This design immobilizes the patient's heel to prevent pressure sores and other soft tissue injuries which typically occur in bedridden patients. As shown in FIG. 14, the upper unit 10 may include a lattice of windows 102 which provide for easy viewing of any soft tissue injuries to the heel from the rear of the device, and provide structural strength. As shown in FIG. 15, upper unit 10 may also include an access panel 104 to allow rear access to the heel for dressing any injuries to the patient's heel area. Access panel 104 may be attached to upper unit 10 at panel hinge 106, and have a catch 108 which may be received by catch receiving point 110. The upper unit 10 also has a flex area 112 that is designed to bend under pressure while a patient is ambulating.

Rigid insert 114 has insert protrusions 116 which may snap into insert-receiving holes 118 to reduce the ability of flex area 112 to bend under pressure. Use of the rigid insert 114 is desirable for bedridden patients that experience contractures in the lower leg and may need a stiffer upper unit 10 for effective pressure therapy.

Figure 1:
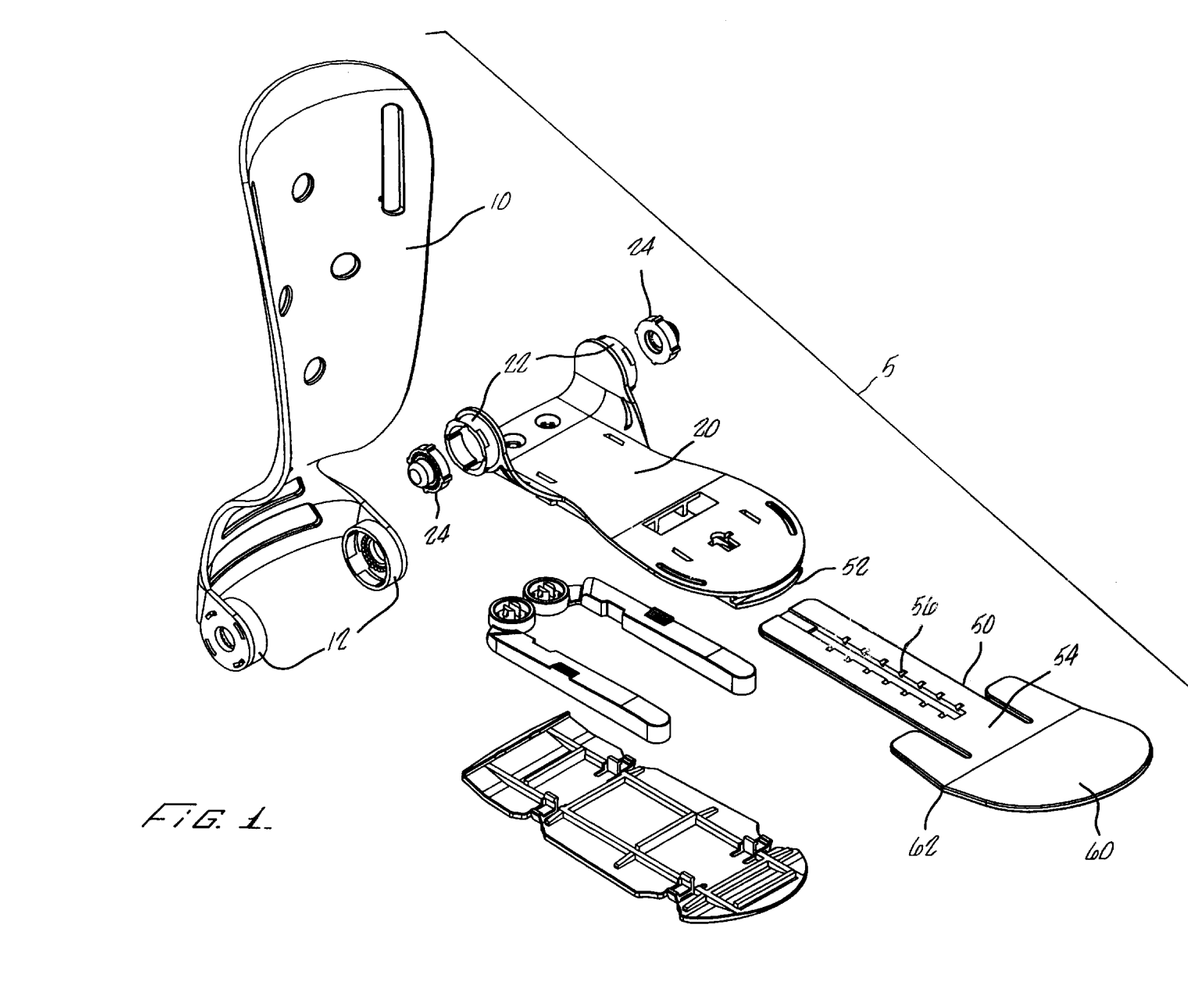
FIG. 1 is an exploded view of the entire orthosis.
Figure 2:
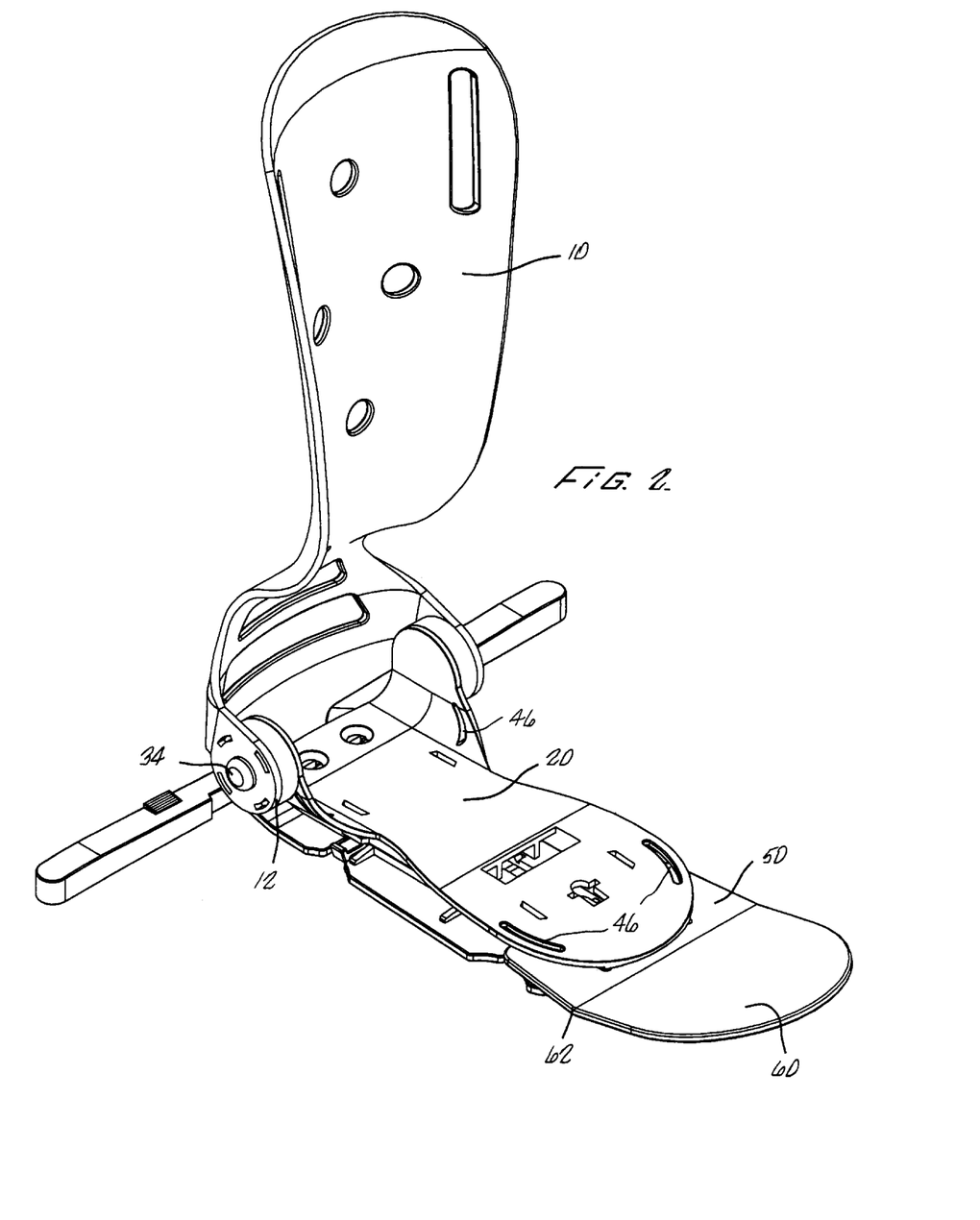
FIG. 2 is a perspective view of an assembled orthosis.
Figure 3:
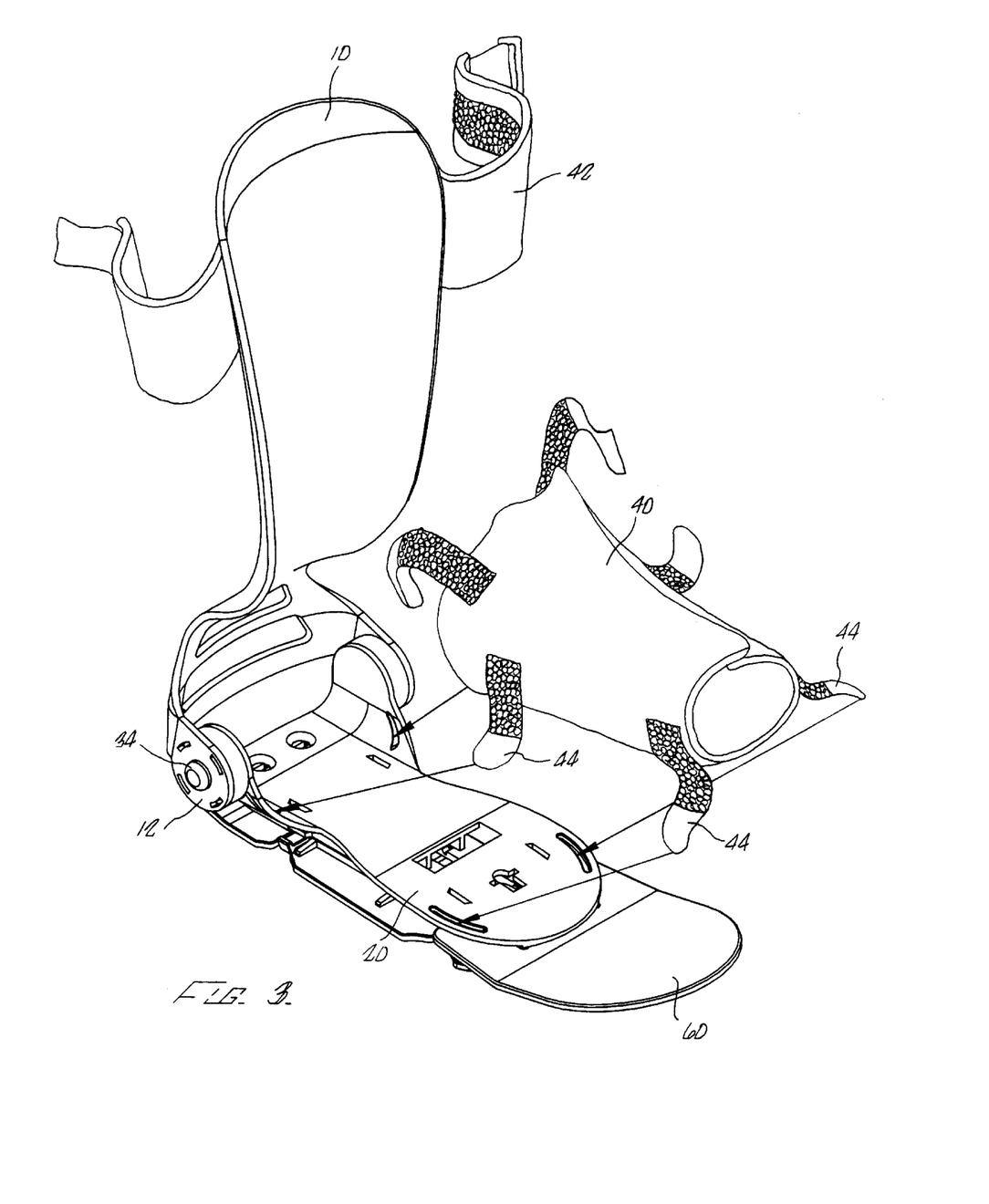
FIG. 3 is a perspective view of the orthosis with a softgood and attachment strap.
Figure 4:
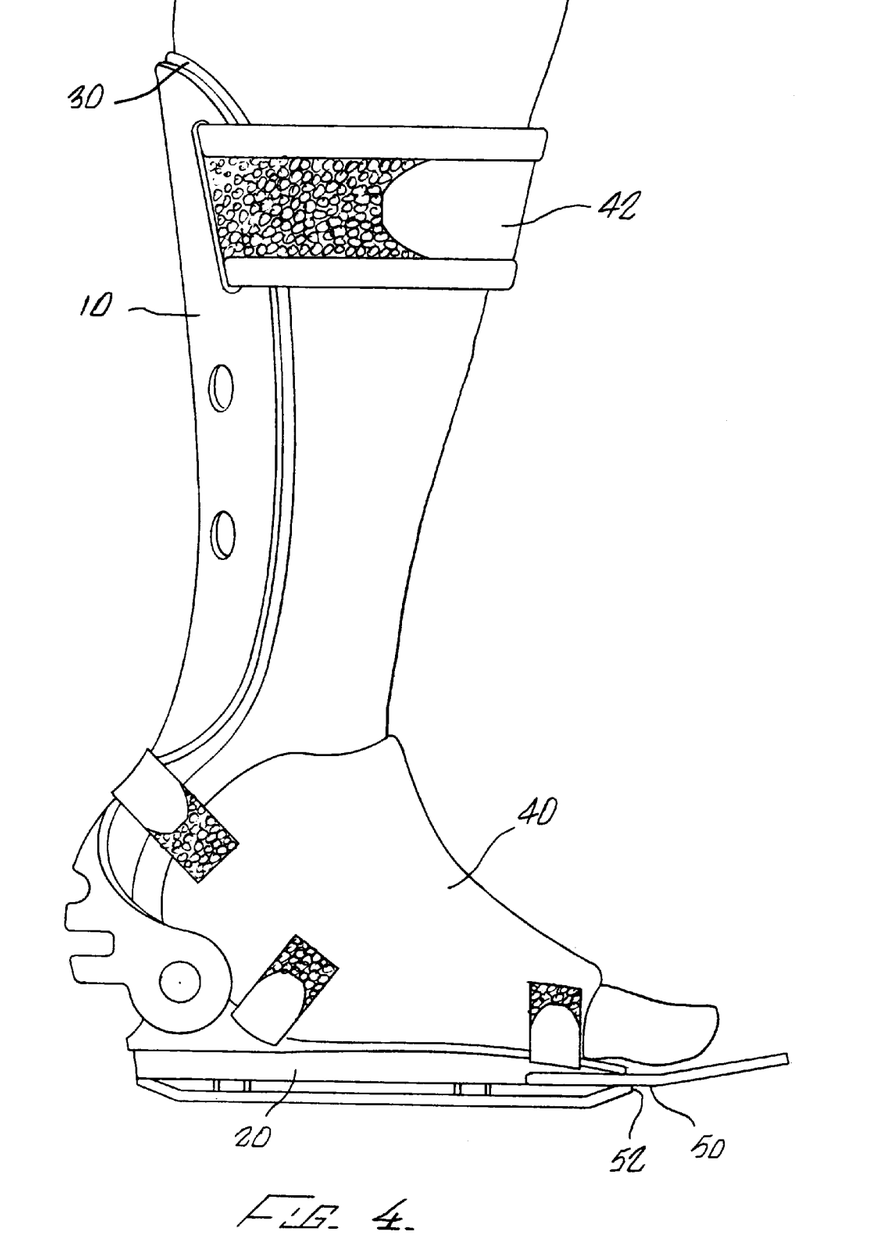
FIG. 4 is a side view of the orthosis in use with a softgood and attachment strap.

Referring now to FIGS. 3 and 4, a softgood is shown which may be used to provide greater comfort for the patient and protection against pressure sores. The softgood may comprise two components, an upper softgood 42 that may wrap around the lower leg of the patient, and foot base unit softgood 40. As shown in FIGS. 16 and 16a, also disclosed is a pneumatic bladder 30 or pad which may be comprised of a plastic film layer 122, an inner open cell foam 124 and an outer material 126 such as brushed nylon. An additional outer layer such as lambs wool or similar material may wrap over the lower leg and be fastened by the use of straps as shown in FIG. 4. The pneumatic bladder 30, by conforming to the irregularities of the patient's lower legs, reduces peak contact pressures and redistributes forces more evenly over the patient's calf, lower leg and foot, thereby greatly reducing the risk of pressure sores for bedridden patients. The foot base unit softgood 40 preferably fits beneath and around the foot to secure the patient's foot to the foot base unit 20 of the orthosis.

Thus a multi-function orthosis for the foot, heel, ankle and lower leg, which provides three-dimensional immobilization, adjustable therapeutic benefits and which allows for ambulation of the human patient is shown and described. Though certain examples and advantages and modifications may be obvious to those skilled in the art from the disclosure herein, the current invention is not to be limited except in the spirit of the claims that follow.

I claim:

1. An orthotic device for use with a human patient, comprising:

a substantially inflexible leg unit;

a substantially inflexible foot base unit; and an adjustable, rotary, angular flexion hinge, said hinge rotatably adjustably attaching said leg unit to said foot base unit, said hinge comprising left and right hinges aligned with each other, and at least one of said left and right hinges comprising:

an upper unit gear fixedly attached to said leg unit;

a middle gear coaxial with and securely engageable with said upper unit gear;

a middle gear receiving means for receiving and holding said middle gear in a fixed angular relationship with respect to said foot base unit, said receiving means being fixedly attached to said foot base unit, and a disengagement means for allowing a user to selectively disengage said middle gear from said upper unit gear and then reengage said middle gear after the user has rotated said gears into the desired angular relationship with respect to each other, wherein said disengagement means includes a readily accessible button and a spring aligned with the axis of said middle gear.

2. An orthotic device for use with a human patient, comprising:

a substantially inflexible leg unit;

a substantially inflexible foot base unit; and a kickstand pivotally attached to said foot base unit and formed to retract flushly into a recess in said foot base unit such that said kickstand presents no appreciable external profile when not in use.

\* \* \* \* \*